United States Patent [19]  [11] 4,155,944
Seidov et al.  [45] May 22, 1979

[54] PROCESS FOR PREPARING ALKYLBENZENES

[76] Inventors: Nadyr M. O. Seidov, ulitsa Nizami 47, kv. 7; Mark A. Dalin, prospekt Kirova 21, kv. 41; Amir-Mamed A. O. Bakhshi-Zade, ulitsa Fabritsiusa 2, kv. 22; Sabir M. O. Kyazimov, ulitsa Kadyrly 6, kv. 2; Tair A. O. Kuliev, ulitsa Rezervuarnaya 4, kv. 54; Valentina V. Lobkina, 17 Zavokzalnaya 19a, kv. 15; Gennady A. Reitman, ulitsa Schorsa 153/155; Julia N. Pshik, ulitsa Nizami 119, kv. 15; Kasum G. O. Kasumov, ulitsa Inglab 100, kv. 32, all of Baku, U.S.S.R.

[21] Appl. No.: 697,822

[22] Filed: Jun. 21, 1976

[51] Int. Cl.² ............................................. C07C 3/56
[52] U.S. Cl. ..................................... 585/457; 585/461
[58] Field of Search ........................ 260/671 C, 671 R

[56] References Cited

U.S. PATENT DOCUMENTS

| | | | |
|---|---|---|---|
| 2,270,292 | 1/1942 | Grosse | 260/683.57 X |
| 2,388,428 | 11/1945 | Mavity | 260/683.57 |
| 2,948,763 | 8/1960 | Ashmore | 260/671 R |
| 3,312,748 | 4/1967 | Johnson | 260/671 R |
| 3,666,825 | 5/1972 | Torck | 260/671 R |
| 3,875,249 | 4/1975 | Nelson | 260/671 R X |

OTHER PUBLICATIONS

Buehler et al., Survey of Organic Synthesis, Wiley Interscience, 1970, p. 34.
Uhlig, Chemical Abstracts 49:5192a.

Primary Examiner—Delbert E. Gantz
Assistant Examiner—J. Thierstein
Attorney, Agent, or Firm—Lackenbach, Lilling & Siegel

[57] ABSTRACT

A process for preparing alkylbenzenes, which comprises alkylation of benzene or alkylderivatives thereof with olefines in the presence of a catalyst comprising a product prepared by reacting metallic aluminum with a chlorinated hydrocarbon in a medium of benzene or an alkylbenzene at a weight ratio between metallic aluminum and said chlorinated hydrocarbon ranging from 1:0.08 to 1:17 respectively; said alkylation being conducted at a temperature within the range of from 50° to 180° C. under a pressure within the range of from 2 to 20 atm. The catalyst employed in the process according to the present invention is non-hygroscopic; it is prepared by rather simple technology; said catalyst ensures a high yield of the desired products (up to 80-96% as calculated for the reacted olefine) while retaining a high quality thereof (for example, purity degree of ethylbenzene prepared thereon is 99.9179% by weight). The alkylbenzenes prepared according to the present invention are valuable stock materials for the production of styrene, alpha-methylstyrene and the like.

4 Claims, No Drawings

PROCESS FOR PREPARING ALKYLBENZENES

The present invention relates to processes for preparing alkylbenzenes which serve as the starting material for the preparation of styrene, alpha-methylstyrene and the like.

Known in the art is a process for preparing alkylbenzenes by alkylation of benzene or alkylderivatives thereof with olefines in the presence of a catalyst, viz. aluminium chloride.

Aluminium chloride supply into a reactor is encountered with certain technological difficulties due to its hygroscopicity. Furthermore, the use of this catalyst results in producing alkylbenzenes in a low yield and having insufficiently high quality.

It is an object of the present invention to provide such a process for preparing alkylbenzenes, wherein use could be made of a non-hygroscopic catalyst.

It is another object of the present invention to provide such a process for preparing alkylbenzenes, wherein use could be made of a catalyst produced by a simple technology.

A further object of the present invention is to provide such a process for preparing alkylbenzenes, wherein use could be made of a catalyst ensuring a high yield of the desired products at a high quality thereof.

These and other objects of the present invention are accomplished by a process for preparing alkylbenzenes by way of alkylation of benzene or alkylderivatives thereof with olefines in the presence of a catalyst; therewith, in accordance with the present invention, as the catalyst use is made of a product prepared by reacting metallic aluminium with a chlorinated hydrocarbon in a medium of benzene or an alkylbenzene at a weight ratio between said metallic aluminium and chlorinated hydrocarbon equal to 1:0.08–17 respectively; the alkylation being conducted at a temperature ranging between 50° and 180° C. under a pressure within the range of from 2 to 20 atm.

Most available is a catalyst comprising a reaction product of metallic aluminium and carbon tetrachloride or an incompletely chlorinated hydrocarbon in a medium of benzene or an alkylbenzene.

The catalyst employed in the process according to the present invention is non-hygroscopic, readily transportable, ensuring a high yield of the desired products (within the range of from 80 to 96% as calculated for the reacted olefine) and a top quality thereof (for example, purity grade of ethylbenzene is 99.9179% of weight).

The process for preparing alkylbenzenes according to the present invention can be performed both periodically and continuously. The following is an embodiment of the process according to the invention.

Into an autoclave metallic aluminium is charged in the form of chips, granules, rods, discs or powder. Afterwards, a solution of a chlorinated hydrocarbon in benzene or an alkylbenzene is added thereto. Temperature in the autoclave is maintained within the range of from 50° to 180° C. and olefine is fed into said reactor to a pressure of from 2 to 20 atm. The autoclave contents is maintained under the above-described conditions.

The catalyst employed in the process according to the present invention can be prepared either in the alkylation-reaction zone under the alkylation conditions (mentioned hereinbefore) or outside the reaction zone of alkylation, at elevated temperatures similar to those of the alkylation reaction. In the latter case the catalyst is prepared in a separate column-type apparatus using the above-mentioned starting components. Then the thus-prepared catalyst is charged into an autoclave in specified amounts, whereinto benzene or an alkylderivative thereof is charged (e.g. toluene) along with olefine. Temperature in the autoclave is maintained within the range of from 50° to 180° C. and a pressure of from 2 to 20 atm and the autoclave contents is maintained under the above-described conditions.

In the process according to the present invention as the incompletely chlorinated hydrocarbons use is made of incompletely chlorinated paraffin hydrocarbons such as chloroform, ethylchloride, dichloroethane, isopropylchloride, isopropyltrichloride, isobutylchloride; incompletely chlorinated hydrocarbons of the naphthenic and aromatic series such as cyclohexylchloride, cyclohexyltrichloride, chlorobenzene, dichlorobenzene, benzylchloride.

For a better understanding of the present invention the following specific Examples illustrating preparation of alkylbenzenes on the above-mentioned catalyst are given hereinbelow.

EXAMPLE 1

Metallic aluminium in the form of a disc with the weight of 50 g is fastened to a stirrer of a 2-lit. autoclave provided with a thermocouple, an inlet pipe for ethylene and benzene. Thereafter, the autoclave is carefully purged with ethylene at the temperature of 200° C. for 1 to 1.5 hour. Then, the autoclave temperature is brought to 70° C.; a solution of 4 g of carbontetrachloride in 400 g of dried benzene is then added into the autoclave and ethylene is supplied thereinto to the pressure of 10 atm. On completion of the experiment (20 minutes after), the autoclave is cooled to room temperature and the pressure is released.

The amount of thus-prepared alkylate is 470 g. The alkylate is subjected to chromatographic analysis. The alkylate has the following composition, per cent;

| | |
|---|---|
| benzene | 42.0 |
| ethylbenzene | 48.0 |
| di- and poly-alkylbenzenes (PAB) | 10.0 |

Conversion of ethylene to ethylbenzene is 90%.

EXAMPLE 2

Alkylation is conducted in a manner similar to that described in the foregoing Example 1. Charged into an autoclave are 40 g of metallic aluminium and a solution of 4 g of carbon tetrachloride in 400 g of benzene. The reaction zone temperature is 100° C., pressure — 12 atm. The amount of ethylene absorbed during 10 minutes is 30 g. The alkylate amount is 430 g. The alkylate composition is as follows (by chromatographic analysis), per cent:

| | |
|---|---|
| benzene | 75.0 |
| ethylbenzene | 23.0 |
| di- and PAB | 2.0 |

Conversion of ethylene to ethylbenzene is 90%.

EXAMPLE 3

Alkylation is conducted in a manner similar to that described in the foregoing Example 1. Into an autoclave there are charged 10 g of metallic aluminium and a solution of 20 g of carbon tetrachloride in 400 g of benzene. The reaction zone temperature is 100° C.; pressure is 12 atm. The amount of ethylene absorbed for 10 minutes is 70 g. The alkylate amount is 495 g. The alkylate composition according to the data of chromatographic analysis is the following, per cent:

| | |
|---|---|
| benzene | 40.0 |
| ethylbenzene | 51.0 |
| di- and PAB | 9.0 |

Conversion of ethylene to ethylbenzene is 85%.

EXAMPLE 4

Alkylation is conducted in a manner similar to that described in the foregoing Example 1. Into an autoclave there are charged 50 g of metallic aluminium and a solution of 50 g of carbon tetrachloride in 400 g of benzene. The reaction zone temperature is 100° C., pressure 15 atm. The amount of ethylene absorbed for 10 minutes is 150 g. The alkylate amount is 600 g. The alkylate composition as determined by chromatographic analysis is the following, per cent:

| | |
|---|---|
| benzene | 10.0 |
| ethylbenzene | 21.0 |
| di- and PAB | 69.0 |

Conversion of ethylene to ethylbenzene is 22%.

EXAMPLE 5

Alkylation is conducted in a manner similar to that described in the foregoing Example 1. Into an autoclave there are charged 40 g of metallic aluminium and a solution of 4 g of carbon tetrachloride in 400 g of benzene. The reaction zone temperature is 150° C., ethylene pressure 20 atm, experiment duration is 60 minutes. The alkylate amount is 508 g.

The alkylate composition as determined by chromatographic analysis is as follows, per cent:

| | |
|---|---|
| benzene | 20 |
| ethylbenzene | 45 |
| di- and PAB | 35 |

Conversion of ethylene to ethylbenzene is 48%.

EXAMPLE 6

Alkylation is conducted in a manner similar to that described in Example 1 hereinabove. Into an autoclave there are charged 50 g of metallic aluminium in the form of chips and a solution of 4 g of carbon tetrachloride in 400 g of benzene. The reaction zone temperature is 70° C., ethylene pressure is 10 atm; experiment duration is 30 minutes. The alkylate amount is 475 g. The alkylate composition as determined by chromatographic analysis is as follows, per cent:

| | |
|---|---|
| benzene | 41.0 |
| ethylbenzene | 46.0 |
| di- and PAB | 13.0 |

Conversion of ethylene to ethylbenzene is 77%.

EXAMPLE 7

Alkylation is conducted in a manner similar to that described in Example 1 hereinabove. Into an autoclave there are charged 40 g of metallic aluminium and a solution of 4 g of carbon tetrachloride in 250 g of toluene. The reaction zone temperature is 100° C.; ethylene pressure is 15 atm; experiment duration is 30 minutes. The alkylate amount is 330 g.

The alkylate composition as determined by chromatographic analysis is the following, per cent:

| | |
|---|---|
| toluene | 10.0 |
| ethyltoluene | 47.0 |
| diethyltoluene | 43.0 |

Conversion of ethylene to ethyltoluene is 45%.

EXAMPLE 8

Into a 1-lit autoclave there are charge 1 g of metallic aluminium and a solution of 17 g of carbon tetrachloride in 400 g of benzene; the autoclave is previously thoroughly dried. At the temperature of 50° C. in the autoclave, ethylene is added thereinto to the pressure of 5 atm. As the pressure is decreasing, fresh ethylene being fed into the autoclave. On completion of the experiment (60 minutes after) the autoclave is cooled to room temperature and the pressure is released. The alkylate amount is 450 g. The alkylate composition as determined by chromatographic analysis is the following, per cent:

| | |
|---|---|
| benzene | 75.4 |
| ethylbenzene | 20.5 |
| di- and PAB | 4.1 |

Conversion of ethylene to ethylbenzene is 65.7

EXAMPLE 9

Alkylation is conducted in a manner similar to that described in the foregoing Example 1, except that ethylene pressure is brought up to 10 atm and the experiment is carried out at the temperature of 70° C. The alkylate amount is 528 g. The alkylate composition as determined by chromatographic analysis is the following, per cent:

| | |
|---|---|
| benzene | 25.5 |
| ethylbenzene | 60.0 |
| di- and PAB | 14.5 |

Conversion of ethylene to ethylbenzene is 72%.

EXAMPLE 10

Alkylation of benzene with ethylene is conducted in a continuous-action autoclave with a capacity of 3 lit provided with a thermocouple, an inlet pipe for benzene and ethylene.

Metallic aluminium in the form of a 40 g-weight disc is secured to the autoclave stirrer. Thereafter, the autoclave is thoroughly purged with dry ethylene for 1–1.5 hour at the temperature of 200° C. Then, the temperature in said autoclave is brought to 130° C. and benzene containing 0.4% of carbon tetrachloride is added thereinto along with ethylene. Molar ratio between ethylene and benzene is 1:3. Pressure in the autoclave is 5 atm. The contact time is 30 minutes. Therewith, consumption of ethylene is 156 g and that of benzene is 1320 g.

The resulting alkylate has the following composition as determined by chromatographic analysis, per cent:

| | |
|---|---|
| benzene | 60.3 |
| ethylbenzene | 38.0 |
| di- and PAB | 1.7 |

Conversion of ethylene to ethylbenzene is 96.5%.

EXAMPLE 11

Into a column-type apparatus with the diameter of 70 mm made of stainless steel there is charged 1 lit of aluminium packing in the form of pieces of aluminium wire with the diameter of 2 mm and 3 mm in length and benzene is supplied into said apparatus at the rate of 2.64 kg/hr, the benzene containing 20% of carbon tetrachloride. The apparatus is operated under atmospheric pressure at the temperature of 70° C. The resulting catalyst is discharged from the bottom section of the apparatus.

Into an autoclave for alkylation there are charged 400 g of benzene and 10 g of the catalyst prepared as above. Then ethylene is fed into the autoclave in the amount of 50 g. Temperature in the autoclave is 130° C.; pressure - 9 atm. On expiration of 9 minutes the alkylate is drained out of the bottom section of the autoclave.

The alkylate composition as determined by chromatographic analysis is the following, per cent:

| | |
|---|---|
| benzene | 60.0 |
| ethylbenzene | 33.1 |
| di- and PAB | 4.9 |

Conversion of ethylene to ethylbenzene is 84%.

EXAMPLE 12

Alkylation is conducted in much the same manner as that described in the foregoing Example 1. Into an autoclave there are charged 2 g of metallic aluminium and a solution of 10 g of carbon tetrachloride in 400 g of benzene. The reaction zone temperature is 100° C., pressure - 12 atm. The amount of ethylene absorbed for 10 minutes is 32 g. The alkylate amount is 432 g.

The alkylate has the following composition as determined by chromatographic analysis, per cent:

| | |
|---|---|
| benzene | 73.0 |
| ethylbenzene | 25.0 |
| di- and PAB | 2.0 |

Conversion of ethylene to ethylbenzene is 91%.

EXAMPLE 13

Alkylation is performed in a manner similar to that described in Example 1 hereinabove. Into an autoclave there is charged 1 g of metallic aluminium and a solution of 10 g of carbon tetrachloride in 400 g of benzene. The reaction zone temperature is 100° C.; propylene pressure is 5 atm. The amount of propylene absorbed for 10 minutes is 96 g. The alkylate amount is 502 g.

The alkylate has the following composition as determined by chromatographic analysis, per cent:

| | |
|---|---|
| benzene | 49.3 |
| isopropylbenzene | 42.5 |
| di- and PAB | 8.2 |

Conversion of propylene to isopropylbenzene is 80%.

EXAMPLE 14

Alkylation is performed in a manner similar to that described in the foregoing Example 1. Into an autoclave there are charged 20 g of metallic aluminium and a solution of 10 g of carbon tetrachloride in 400 g of benzene. The reaction zone temperature il 100° C.; butylene pressure is 5 atm. The amount of butylene absorbed for 30 minutes is 27 g. The alkylate amount is 430 g.

EXAMPLE 15

Into a 2-lit. autoclave provided with a thermocouple, an inlet pipe for the supply of benzene and ethylene, there is charged metallic aluminium in the form of a 25g-weight disc. Thereafter, the autoclave is carefully purged with ethylene at the temperature of 200° C. for 1-1.5 hour, whereafter the temperature in the autoclave is reduced to 100° C. Then, poured into the autoclave is a solution of 12 g of ethyl chloride in 400 g of dried benzene and ethylene is fed to the autoclave pressure of 10 atm. The pressure in the autoclave is maintained constant. The reaction zone temperature is 100° C.; experiment duration is 10 minutes. Thereafter, the autoclave is cooled to room temperature and the pressure is released.

The alkylate amount is 482 g. The amount of ethylene absorbed is 78 g. The alkylate is subjected to chromatographic analysis. The alkylate composition, as determined by the chromatographic analysis, is the following, per cent:

| | |
|---|---|
| benzone | 40 |
| ethylbenzene | 55.8 |
| di- and PAB | 4.2 |

Conversion of ethylene to ethylbenzene is 91%.

EXAMPLE 16

Alkylation is performed in a manner similar to that described in the previous Example 15. Into an autoclave there are charged 20 g of metallic aluminium and a solution of 4 g of ethyl chloride in 400 g of benzene is added thereto. The experiment duration is 10 minutes.

The amount of ethylene absorbed is 33 g. The alkylate amount is 446 g. The alkylate composition as determined by chromatographic analysis is the following, per cent:

| | |
|---|---|
| benzene | 71.0 |
| ethylbenzene | 26.5 |
| di- and PAB | 2.5 |

Conversion of ethylene to benzene is 86.9%.

EXAMPLE 17

Alkylation is conducted in a manner similar to that described in the foregoing Example 15. Into an autoclave there are charged 10 g of metallic aluminium and 12 g of isopropylchloride dissolved in 400 g of benzene. Propylene is fed into the autoclave to the pressure of 5 atm. The pressure drop is compensated by adding a new portion of fresh propylene. The reaction zone temperature is 100° C. The experiment duration is 10 minutes. The amount of propylene absorbed is 94 g. The alkylate amount is 500 g. The alkylate composition as determined by chromatographic analysis is the following, per cent:

| | |
|---|---|
| benzene | 49.3 |
| isopropylbenzene | 44.5 |
| di- and PAB | 6.2 |

Conversion of propylene to isopropylbenzene is 81.7%.

EXAMPLE 18

Alkylation is effected in a manner similar to that described in Example 15 hereinbefore. Into an autoclave there are charged 10 g of metallic aluminium and 4 g of isopropylchloride dissolved in 400 g of benzene. Propylene is then admitted into the autoclave to the pressure of 5 atm. The reaction zone temperature is 100° C. The experiment duration is 10 minutes. The amount of propylene absorbed is 78 g. The alkylate amount is 492 g. The alkylate composition as determined by chromatographic analysis is the following, per cent:

| | |
|---|---|
| benzene | 52.4 |
| isopropylbenzene | 42.0 |
| di- and PAB | 5.6 |

Conversion of propylene to isopropylbenzene is 83.5%.

EXAMPLE 19

Alkylation is performed in a manner similar to that described in Example 15 hereinbefore. Into an autoclave there are charged 5 g of metallic aluminium and 12 g of cyclohexylchloride dissolved in 400 g. of benzene. Into the autoclave ethylene is admissed to the pressure of 5 atm. The reaction zone temperature is 130° C. The experiment duration is 10 minutes. The amount of ethylene absorbed is 54 g. The alkylate amount is 465 g. The alkylate composition as determined by chromatographic analysis is the following, per cent:

| | |
|---|---|
| benzene | 58.5 |
| ethylbenzene | 36.5 |
| di- and PAB | 5.0 |

Conversion of ethylene to ethylbenzene is 82.6%.

EXAMPLE 20

Alkylation is conducted in a manner similar to that described in Example 15 hereinbefore. Into an autoclave there are charged 10 g of metallic aluminium and 4 g of cyclohexylchloride dissolved in 400 g of benzene. Ethylene is then admitted into the autoclave to the pressure of 5 atm. The reaction zone temperature is 130° C. The experiment duration is 10 minutes. The amount of ethylene absorbed is 62.4 g. The alkylate amount is 480 g. The alkylate has the following composition as determined by chromatographic analysis, per cent:

| | |
|---|---|
| benzene | 52.1 |
| ethylbenzene | 40.0 |
| di- and PAB | 7.9 |

Conversion of ethylene to ethylbenzene is 81%.

EXAMPLE 21

Alkylation is conducted in a manner similar to that described in Example 15 hereinbefore. Charged into an autoclave are 4 g of metallic aluminium and 12 g of benzylchloride dissolved in 400 g of benzene. Ethylene is then admissed into the autoclave to the pressure of 5 atm. The reaction zone temperature is 130° C. The experiment duration is 10 minutes. The amount of ethylene absorbed is 62 g. The alkylate amount is 472 g. Alkylate has the following composition as determined by chromatographic analysis, per cent:

| | |
|---|---|
| benzene | 53.5 |
| ethylbenzene | 40.0 |
| di- and PAB | 6.5 |

Conversion of ethylene to ethylbenzene is 84%.

EXAMPLE 22

Alkylation is conducted in a manner similar to that described in Example 15 hereinbefore. Into an autoclave there are charged 10 g of metallic aluminium and 12 g of ethylchloride dissolved in 400 g of toluene. Ethylene is then admissed into the autoclave to the pressure of 5 atm. The reaction zone temperature is 130° C. The experiment duration is 10 minutes. The amount of ethylene absorbed is 54 g. The alkylate amount is 464 g. The alkylate composition as determined by chromatographic analysis is the following, per cent:

| | |
|---|---|
| toluene | 51.6 |
| ethyltoluene | 42.8 |
| diethyltoluene | 5.6 |

Conversion of ethylene to ethyltoluene is 83.5%.

EXAMPLE 23

Into a column-type apparatus with the diameter of 70 mm made of stainless steel there are charged 2 l of aluminium packing (bulk weight 1.495 g/cm$^3$) comprising pieces of aluminium wire cut to lengths of 4 mm and 2 mm diameter and benzene is admissed thereinto in the amount of 1.2 kg/hr. Vapours of ethyl chloride are passed into the apparatus through a grate located in the bottom section thereof at the rate of 1.2 kg/hr. The apparatus is operated under atmospheric pressure and at the temperature of 60° C. The resulting catalyst produced at the rate of 1.8 kg/hr is discharged out of the bottom section of the apparatus.

Into an autoclave for alkylation there are charged 400 g of benzene and 4 g of the catalyst prepared as above. Then, ethylene is admitted into the autoclave in the amount of 48 g. The autoclave is operated at the temperature of 130° C. under the pressure of 9 atm. On expiration of 10 minutes the alkylate is drained from the bottom section of the autoclave.

The alkylate has the following composition as determined by chromatographic analysis, per cent:

| | |
|---|---|
| benzene | 61.7 |
| ethylbenzene | 32.4 |
| di- and PAB | 4.9 |

Ethylene conversion to ethylbenzene is 81%.

EXAMPLE 24

Alkylation is conducted in a manner similar to that described in Example 15 hereinbefore. Into an autoclave there are charged 20 g of metallic aluminium and a solution of 20 g of ethylchloride in 400 g of benzene is added thereto. Then, ethylene is admitted into the autoclave. The reaction zone temperature is 60° C. The autoclave is operated under the pressure of 2 atm. The experiment duration is 60 minutes. Thereafter, the autoclave is cooled to room temperature.

The amount of ethylene absorbed is 32 g. The alkylate amount is 447 g. The alkylate composition as determined by chromatographic analysis is the following, per cent:

| benzene | 73.0 |
|---|---|
| ethylbenzene | 24.6 |
| di- and PAB | 2.4 |

Conversion of ethylene to ethylbenzene is 87%.

EXAMPLE 25

Alkylation is conducted is a manner similar to that described in Example 15 hereinbefore. Into an autoclave there are charged 2 g of metallic aluminium and 10 g of isobutylchloride dissolved in 400 g of benzene. Then, ethylene is fed into the autoclave. The reaction zone temperature is 180° C., pressure in the autoclave is 20 atm. The experiment duration is 5 minutes. The amount of ethylene absorbed is 76 g. The alkylate amount is 480 g. The alkylate composition as determined by chromatographic analysis is the following, per cent:

| benzene | 40.0 |
|---|---|
| ethylbenzene | 48.2 |
| di- and PAB | 11.8 |

Conversion of ethylene to ethylbenzene is 75%.

EXAMPLE 26

The catalyst is prepared by the procedure similar to that described in the foregoing Example 23. Into an apparatus there is charged 1 litre of aluminium packing and benzene is supplied thereinto at the rate of 0.6 kg/hr. Through a grate in the bottom section of the apparatus vapours of ethylchloride are fed at the rate of 0.6 kg/hr. The temperature in the apparatus is maintained at 180° C. The resulting catalyst produced in the amount of 0.8 kg/hr is discharged from the bottom section of the apparatus.

Into an autoclave for alkylation there are charged 400 g of benzene and 4 g of the catalyst prepared as above. Then, ethylene is admitted into the autoclave in the amount of 48g. The reaction zone temperature is 130° C., pressure - 6 atm. On expiration of 10 minutes the alkylate is drained out of the bottom section of the apparatus.

The alkylate consumption as determined by chromatographic analysis is the following, per cent:

| benzene | 62 |
|---|---|
| ethylbenzene | 32.1 |
| di- and PAB | 4.9 |

Conversion of ethylene to ethylbenezene is 80%.

EXAMPLE 27

The catalyst is prepared as in Example 23 hereinbefore. Into an apparatus there are charged 2 lit. of aluminium packing and toluene is supplied thereinto at the rate of 1.2 kg/hr. Through a grate in the apparatus bottom section vapours of ethylchloride are fed at the rate of 1.2 kg/hr. Temperature in the apparatus is maintained at 45° C. The catalyst produced in the amount of 1.8 kg/hr is discharged from the bottom section of the apparatus.

Into an autoclave for alkylation there are charged 400 g of toluene and 4 g of the catalyst prepared as above. Then, ethylene is fed into the autoclave in the amount of 53 g. The reaction zone temperature is 130° C., pressure 10 atm. On expiration of 10 minutes the alkylate is drained from the autoclave bottom section. The alkylate composition determined chromatographically is the following, per cent: toluene 52.0; ethyltoluene 42.4; diethyltoluene 5.6.

Conversion of ethylene to ethyltoluene is 83%.

What is claimed is:

1. In a process for the preparation of alkylbenzenes by the catalytic alkylation of benzene or alkyl derivatives thereof, with an olefin, the improvement which consists essentially of forming the catalyst by contacting aluminium with a chlorinated hydrocarbon in a solution of benzene or alkylbenzene, at a temperature ranging from 50°-180° C. and a pressure ranging from 2 - 20 atm., wherein the ratio of aluminium to chlorinated hydrocarbon varies from about 1:0.08 to 1:17, respectively.

2. The process of claim 1 wherein said catalyst is formed in situ, in the alkylation medium.

3. A process in accordance with claim 1, wherein the catalyst is produced by reacting aluminum with carbon tetrachloride as the chlorinated hydrocarbon. aluminum 4. A process in accordance with claim 1 in which the catalyst is prepared by reacting aluminum with a chlorinated hydrocarbon which is an incompletely chlorinated hydrocarbon.

* * * * *